United States Patent [19]
Tachibana et al.

[11] Patent Number: 5,315,998
[45] Date of Patent: May 31, 1994

[54] BOOSTER FOR THERAPY OF DISEASES WITH ULTRASOUND AND PHARMACEUTICAL LIQUID COMPOSITION CONTAINING THE SAME

[76] Inventors: Katsuro Tachibana; Shunro Tachibana, both of 6-18, Kusagae 1-chome, Chuo-ku, Fukuoka-shi, Fukuoka 810, Japan

[21] Appl. No.: 855,545

[22] Filed: Mar. 20, 1992

[30] Foreign Application Priority Data

Mar. 22, 1991 [JP] Japan ................... 3-058970

[51] Int. Cl.$^5$ ............................. A61B 8/00
[52] U.S. Cl. .................... 128/660.01; 424/9
[58] Field of Search .......... 609/22; 128/24 AA, 24 R, 128/667.02, 660.01; 424/2, 9

[56] References Cited

U.S. PATENT DOCUMENTS

| | | | |
|---|---|---|---|
| 4,466,442 | 8/1984 | Hilmann et al. | 128/653.1 |
| 4,657,756 | 4/1987 | Rasor et al. | 128/662.02 |
| 4,774,958 | 10/1988 | Feinstein | 128/660.01 |
| 4,844,882 | 7/1989 | Widder et al. | 128/660.01 |
| 4,900,540 | 2/1990 | Ryan et al. | 128/662.02 |
| 5,149,319 | 9/1992 | Unger | 128/660.01 |

FOREIGN PATENT DOCUMENTS

| | | |
|---|---|---|
| 0327490 | 8/1989 | European Pat. Off. |
| 0278074 | 3/1990 | European Pat. Off. |
| 52115591 | 9/1977 | Japan |
| 2180275 | 7/1990 | Japan |
| WO8905160 | 6/1989 | PCT Int'l Appl. |
| WO9001971 | 3/1990 | PCT Int'l Appl. |
| 1577551 | 10/1980 | United Kingdom |

Primary Examiner—C. Fred Rosenbaum
Assistant Examiner—Michael Rafa
Attorney, Agent, or Firm—Cushman, Darby & Cushman

[57] ABSTRACT

A booster comprising a plenty of microbubbles of a gas in a liquid, e.g. about $4 \times 10^7$ cells/ml of microbubbles of a gas having a diameter of 0.1 to 100 μm in a 3 to 5% human serum albumin solution, and a pharmaceutical liquid composition comprising the booster as set forth above and a medicament, which are useful for the therapy of various diseases together with exposure of ultrasonic, where the therapeutic effects of the medicament is enhanced by the application of ultrasound in the presence of the booster.

16 Claims, 2 Drawing Sheets ically relates to a booster useful for therapy of various
BOOSTER FOR THERAPY OF DISEASES WITH ULTRASOUND AND PHARMACEUTICAL LIQUID COMPOSITION CONTAINING THE SAME This invention relates to a booster useful for enhancing the effects of ultrasound in the therapy of various diseases and a pharmaceutical liquid composition containing the booster and a medicament which shows enhanced diffusion and penetration of the medicament into the body by applying ultrasound. More particularly, it relates to a booster useful for therapy of various disease by applying ultrasound which comprises a plenty of microbubbles of a gas in a liquid, a pharmaceutical liquid composition comprising a plenty of microbubbles of a gas and a medicament in a liquid, and the use thereof in the therapy of various diseases while applying ultrasound.

Prior Art

It is known that various diseases are remedied by the aid of ultrasonic vibration. For example, it is described in Japanese Patent First Publication (Kokai) No. 115591/1977, etc. that percutaneous absorption of a medicament is enhanced by applying a ultrasonic vibration. Japanese Patent First Publication (Kokai) No. 180275/1990 discloses a drug-injecting device which is effective on the diffusion and penetration of the drug by applying a ultrasonic vibration in the step of injecting a drug into a human body via a catheter or a drug-injecting tube. U.S. Pat. Nos. 4,953,565 and 5,007,438 also disclose the technique of percutaneous absorption of medicaments by the aid of ultrasonic vibration. It is also reported that a tumor can be remedied by concentratedly applying ultrasound from outside the body.

In order to enhance the therapeutic effects with ultrasound, it is required to apply a higher energy of a ultrasonic vibration. However, too higher energy of a ultrasonic vibration causes disadvantageously burns or unnecessary heat at the portion other than the desired portion. On the other hand, when the energy of a ultrasonic vibration is lowered for eliminating such disadvantages, there is a problem of less effect of the ultrasound at the desired portion.

SUMMARY DESCRIPTION OF THE INVENTION

The present inventors have intensively studied on the enhancement of the effects of ultrasound with a lower energy of a ultrasonic vibration and have found that a booster comprising a plenty of microbubbles of a gas in a liquid is useful for the desired enhancement of the effects of ultrasound.

An object of the invention is to provide a booster useful for enhancing the effects of ultrasound which comprises a plenty of microbubbles of a gas in a liquid. Another object of the invention is to provide a pharmaceutical liquid composition containing the booster and a medicament which is useful for the therapy of various diseases together with the application of ultrasound. A further object of the invention is to provide a method for enhancing the effects by the application of ultrasound in the therapy of various diseases which comprises injecting the booster or the pharmaceutical liquid composition as set forth above into the portion to be remedied while applying ultrasound thereto. These and other objects and advantages of the invention will be apparent to those skilled in the art from the following description.

DETAILED DESCRIPTION OF THE INVENTION

Figure 2:
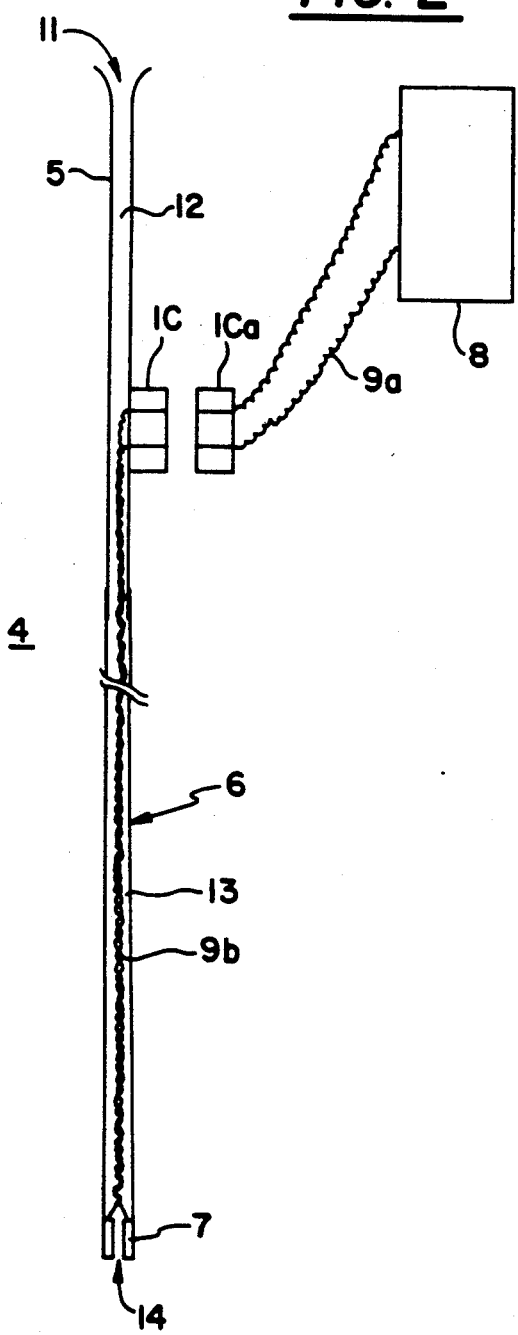
FIG. 2 shows a schematic sectional view of one embodiment of a drug administration device used for injecting, pouring, applying or circulating the booster or the pharmaceutical liquid composition of the invention.

The booster of the invention comprises a liquid containing a plenty of microbubbles of a gas having a diameter of 0.1 to 100 μm. The microbubbles are formed by entrapping microspheres of a gas into a liquid. The booster contains, for example, about $4 \times 10^7$ of the microbubbles per one milliliter of a liquid. The microbubbles are made of various gases such as air, oxygen gas, carbon dioxide gas, inert gases (e.g. xenon, krypton, argon, neon, helium, etc.), preferably air and oxygen gas. The liquid includes any liquid which can form microbubbles, for example, human serum albumin (e.g. 3 to 5% human serum albumin), a physiological saline solution, a 5% aqueous glucose solution, an aqueous indocyanine green solution, autoblood, an aqueous solution of maglumine diatriazoate (=renografin), and any other X-ray contrast medium.

The booster can be prepared by a known method, for example, by agitating the liquid as mentioned above while blowing a gas as mentioned above into the liquid, or alternatively exposing the liquid to ultrasound with a sonicator under a gaseous atmosphere, whereby a vibration is given to the liquid to form microbubbles of the gas.

The pharmaceutical liquid composition of the invention comprises a plenty of microbubbles of a gas and a medicament in a liquid. The microbubbles of a gas and liquid are the same as mentioned above. The medicament includes any known medicaments effective for the desired therapy which can be absorbed percutaneously, for example, anti-thrombosis agents (e.g. urakinase, tissue plasminogen activator, etc.), hormones (e.g. insulin, etc.), theophylline, lidocaine, antibiotics, antineoplastic agents which are sensitive to ultrasound (e.g. doxorubicin (=adriamycin), cytarabine (=Ara-C), etc.), and the like. The medicament can be contained in a therapeutically effective amount as usually used. The pharmaceutical liquid composition can be prepared by mixing a medicament with a booster comprising a plenty of microbubbles of a gas in a liquid. The mixing ratio may vary depending on the desired amount and kind of the medicament and the kind of the liquid, but is usually in a range of 1:100 to 100:1 by weight (a medicament/a booster).

According to the invention, the therapeutic effects by ultrasound is boosted by the presence of a booster of the invention. Particularly, when a pharmaceutical liquid composition containing the booster and a medicament is poured or injected into a body in parenteral routes, such as intravenously, percutaneously or intramuscularly, while applying thereto a ultrasonic vibration, the therapeutic effects of the medicament is significantly enhanced. When a ultrasound from a ultrasonic element is applied to the liquid containing the booster and medicament, cavitation occurs in the liquid composition, and the medicament is diffused and penetrated into the desired portion of the biobody by the aid of vibration induced by the cavitation. The cavitation occurs when the level of vibration energy overs a certain threshold value. When the ultrasound is applied to the liquid composition of the invention, the threshold value of the vibration energy lowers due to the presence of a plenty of microbubbles of a gas. That is, the microbubbles of a gas act as nucleus of cavitation and thereby the cavitation occurs more easily. Accordingly, according to the invention, the desired ultrasonic energy necessary for the desired diffusion and penetration of a medicament is achieved even by less energy of ultrasonic vibration energy.

The desired ultrasound is applied by conventional ultrasonic devices which can supply a ultrasonic signal of 20 KHz to several MHz.

With reference to the accompanying drawing, the invention is illustrated in more detail.

Figure 1:
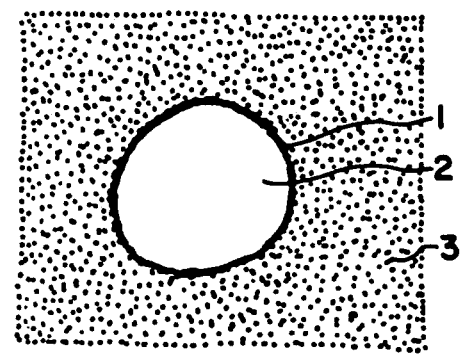
FIG. 1 shows a schematic view of one of the microbubbles contained in the booster of the invention.

FIG. 1 shows a schematic view of one of the plenty of microbubbles of a gas contained in the booster of the invention, wherein the microbubble of a gas has a diameter of 0.1 to 100 μm and is composed of a shell of human serum albumin (1) and gas (2) entrapped within the microbubble. The microbubbles are contained in a liquid (3) such as 5% human serum albumin solution in an amount of, for example, above $4 \times 10^7$ cells/ml.

The booster is mixed with a medicament to give a pharmaceutical liquid composition. The pharmaceutical liquid composition is directly administered to the diseased part with an appropriate device, for example, with a drug administration device (4) as shown in FIG. 2. The drug administration device (4) comprises a base tube (5) to which the pharmaceutical liquid composition is supplied, and an end tube (6) which is to be inserted into the tissue of the biobody and through which the pharmaceutical liquid composition is poured or injected into the diseased part. The end tube (6) is provided with a ultrasonic element (7) (e.g. a cylindrical ceramic oscillator, etc.). The ultrasonic element (7) is supplied by a ultrasonic signal of 20 kHz to several MHz from a ultrasonic oscillation circuit (8) via a conductor (9a), connectors (10a) and (10b) provided on the side of the base tube (5), a part of the base tube (5) and a conductor (9b) provided within the end tube (6).

The application or injection of a medicament is carried out in the form of a pharmaceutical liquid composition which is prepared by previously mixing the medicament with the booster comprising a plenty of microbubbles of a gas in a liquid, wherein the medicament and the booster are mixed in a ratio of 1:100 to 100:1 by weight. The pharmaceutical liquid composition is poured into the base tube (5) from the supply opening (11) provided on the tip of the base tube (5), passes through a flow path (12) within the base tube (5) and a flow path (13) within the end tube (6) and then administered to the diseased part or the portion close thereto of the patient via a pouring opening (14) provided at the bottom of the end tube (6).

When the pharmaceutical liquid composition is administered into the diseased part or the portion close thereto through the pouring opening (14), a ultrasonic energy generated from a ultrasonic element (7) is given to the liquid composition, by which cavitation occurs owing to the ultrasonic energy. Microbubbles are formed at the occurrence of cavitation and when the microbubbles are decomposed, energy is generated, by which diffusion and penetration of the medicament is promoted. Since the pharmaceutical liquid composition contains a plenty of microbubbles of a gas, the microbubbles act as a nucleus for the cavitation, by which the cavitation occurs more easily, in other words, the threshold value of occurrence of cavitation lowers. Accordingly, it is possible to generate the cavitation with less energy than the case of using no booster.

When a ultrasonic vibration is applied to a liquid, if the liquid contains any material being able to become a nucleus, the cavitation occurs generally at a lower threshold value of energy, but it has been found that the cavitation occurs most easily where the liquid contains microbubbles of a gas having a diameter of 0.1 to 100 μm.

The drug administration device (4) as shown in FIG. 2 can be used, for example, for administering a pharmaceutical liquid composition into a blood vessel. For instance, in the treatment of coronary thrombosis, a pharmaceutical liquid composition comprising a booster of the invention and a urokinase is injected into the part of thrombosis or the close portion thereof with the drug administration device (4) where the tip of the end tube (6) is inserted into the portion close to the thrombosis with applying ultrasound, by which the thrombolytic effects of the medicament are significantly increased and further the blood flow is recovered within a shorter period of time in comparison with the administration of the medicament without the booster. The drug administation device (4) may also be used for the removing hematoma in bleeding of brain. For example, a pharmaceutical liquid composition comprising a booster of the invention and a thromolytic agent (e.g. urokinase) is administered to the portion of hematoma with the drug administration device (4) with applying ultrasound like the above, by which the hematoma is easily lysed.

Figure 3:
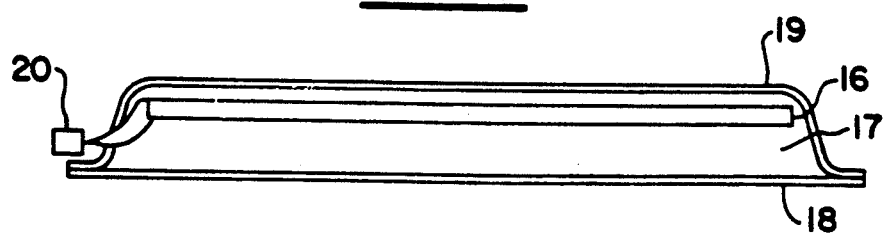
FIG. 3 shows a schematic sectional view of one embodiment of a drug administration device used for percutaneous injection of the booster or the pharmaceutical liquid composition of the invention.

In another embodiment of the invention, the pharmaceutical liquid composition can be administered percutaneously with a drug administration device (15) as shown in FIG. 3.

In the drug administration device (15) suitable for percutaneous administration of a medicament, a layer of a medicament (17) is provided below a ultrasonic element (16) (e.g. a disc shaped ceramic oscillator, etc.), under of which an adhesive layer (18) having a medicament permeability is laminated, whole of which is covered with a plastic cover (19). The ultrasonic element (16) is supplied by ultrasonic signal from a ultrasonic oscillation circuit provided outside via a connector (20) like in the drug administration device (4) as shown in FIG. 2.

In the device (15) of FIG. 3, a pharmaceutical liquid composition comprising a mixture of a booster and a medicament is contained in the layer of a medicament (17). When this device (15) is used, it is adhered onto the skin with facing the adhesive layer (18) to the skin, and then a ultrasonic signal is supplied to the ultrasonic element (16), by which a ultrasonic vibration from the ultrasonic element (16) is given to both of the medicament layer (17) and the skin and thereby the medicament contained in the medicament layer (17) is passed through the skin and is penetrated into the tissue to be treated. In this embodiment, since microbubbles of a gas are contained in the medicament layer (17), cavitation occurs easily within the medicament layer (17) by application of ultrasound, and hence even lower energy of the ultrasonic vibration is supplied from the ultrasonic element (16), the diffusion and penetration of the medicament can effectively be done to result in rapid absorption of the medicament.

The booster of the invention may also be used alone without mixing with a medicament in the therapy with ultrasound. For example, in the therapy of tumors by heating the diseased part of the tissue with ultrasound, that is, by concentratedly applying a ultrasonic vibration outside the biobody, a booster comprising a plenty of microbubbles of a gas in a liquid of the invention is previously injected into the blood vessel or to the portion close to the diseased part before application of ultrasound, by which the effect of heating with ultrasound is enhanced and thereby the therapeutic effects are significantly improved. In this embodiment, cavitation occurs also by the ultrasonic vibration more easily because of using a liquid containing microbubbles of a gas, and hence, even by less energy of the ultrasonic vibration suppled from the ultrasonic element, the ultrasonic energy sufficient to the therapy is obtained and thereby the undesirable burns and unnecessary heating at other portions can be avoided.

In the treatment of tumors, it is, of course, more effective to use it together with a chemotherapeutic agent suitable for the treatment of the tumors, by which the effects of the chemotherapeutic agent are more enhanced, where the diffusion and penetration of the medicament are improved owing to the booster.

The substance such as human serum albumin in the booster of the invention is easily metabolized within the biobody and excreted outside the biobody, and hence, it is not harmful to human body. Besides, the gas trapped within the microbubbles is extremely small and is easily dissolved in the blood fluid. Accordingly, the booster of the invention has no problem in the safety thereof.

The preparation of the booster and pharmaceutical liquid composition of the invention and effects thereof are illustrated by the following Examples and Experiment, but it should not be construed to be limited thereto.

EXAMPLE 1

Preparation of a Booster:

A 5% human serum albumin (8 ml) in a 10 ml-volume syringe is exposed to ultrasound with a sonicator (frequency, 20 KHz) by which vibration is given to the human serum albumin and a plenty of microbubbles of air are formed in the human serum albumin to give a booster comprising a human serum albumin containing a plenty of microbubbles of air.

EXAMPLE 2

Preparation of a Pharmaceutical Liquid Composition:

The 5% human serum albumin containing a plenty of microbubbles of air prepared in Example 1 is mixed with urokinase (concentration 1200 IU/ml) to give the desired pharmaceutical liquid composition.

Experiment

1. Forming Artificial Thrombosis

An artificial thrombosis was formed by Chandler's method. A blood (1 ml) collected from healthy human (two persons) was entered into a flexibale tube (inside diameter 3 mm, length 265 mm) and thereto was added calcium chloride, and then the tube was made a loop like shape, which was rotated at 12 r.p.m. for 20 minutes to give an artificial thrombosis model.

2. Ultrasonic Catheter

A ceramic ultrasonic element (width 2 mm, length 5 mm, thickness 1 mm) was inserted into the tip of a cetheter (diameter 2 mm), and an oscillating element was connected to an oscillator provided outside with a fine connector passed through the catheter. A fine tube for pouring a test solution was provided at an opening opposite to the opening of the catheter end.

3. Test Method

The artificial thrombosis prepared above was added to a test tube together with a blood, and the ultrasonic catheter was inserted into the test tube so that the end of the catheter was set close to the portion of the artificial thrombosis (at a distance of about 5 mm), and to the test tube a mixture of urokinase and a booster prepared in Example 1 was added at a rate of 1 ml per minute, wherein urokinase (concentration 1200 IU/ml) and the booster were mixed immediately before pouring at a mixing ratio of 1:1 by weight. The mixture was refluxed while keeping the volume of the test solution at a constant level by removing excess volume of the solution by suction. The ultrasound (170 KHz) was exposed to the mixture by a pulse method (exposed for 2 seconds and stopped for 4 seconds) for 2 minutes (total exposing time 40 seconds). After the exposure, the ultrasonic catheter was removed from the test tube, and the mixture was incubated at 37° C. for 5 to 120 minutes, washed with a physiological saline solution several times and dried overnight. Thereafter, the dried mixture was weighed. As a control, the above was repeated by using only a physiological saline solution.

4. Test Results

The rate of fibrinolysis was calculated by the following equation:

$$\text{Fibrinolysis rate (\%)} = \frac{\left[\begin{array}{c}\text{Weight of}\\\text{thrombis}\\\text{in control}\end{array}\right] - \left[\begin{array}{c}\text{Weight of}\\\text{thrombosis}\\\text{treated}\end{array}\right]}{\text{Weight of thrombsis in control}} \times 100$$

Figure 4:
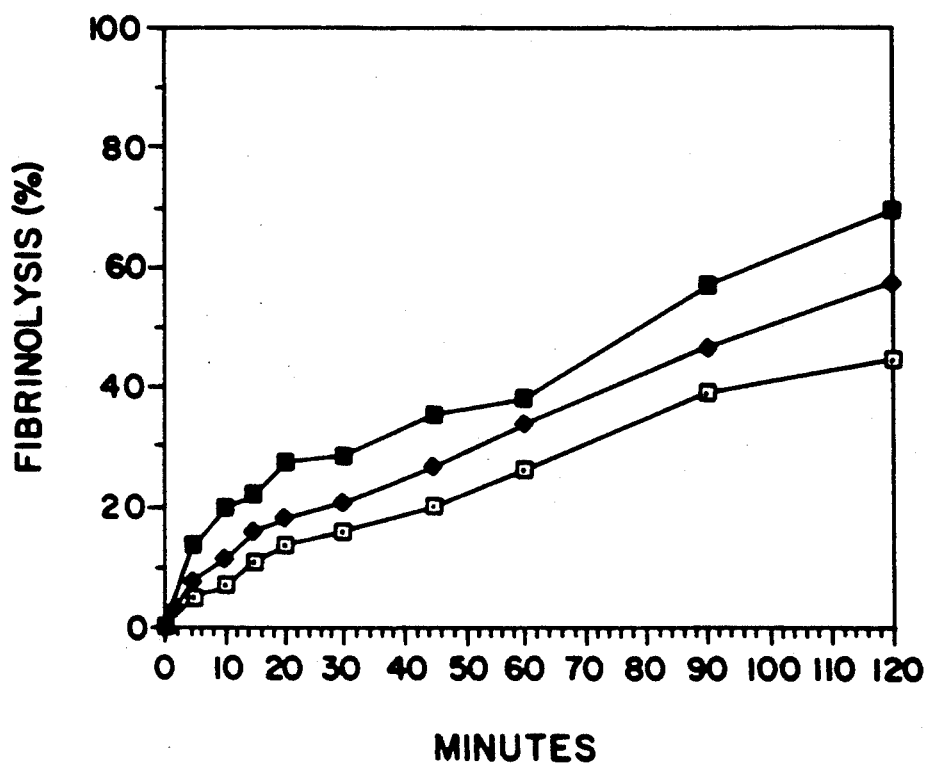
FIG. 4 and FIG. 5 show graphs showing fibrinolysis by application of ultrasound with or without the booster of the invention.
Figure 5:
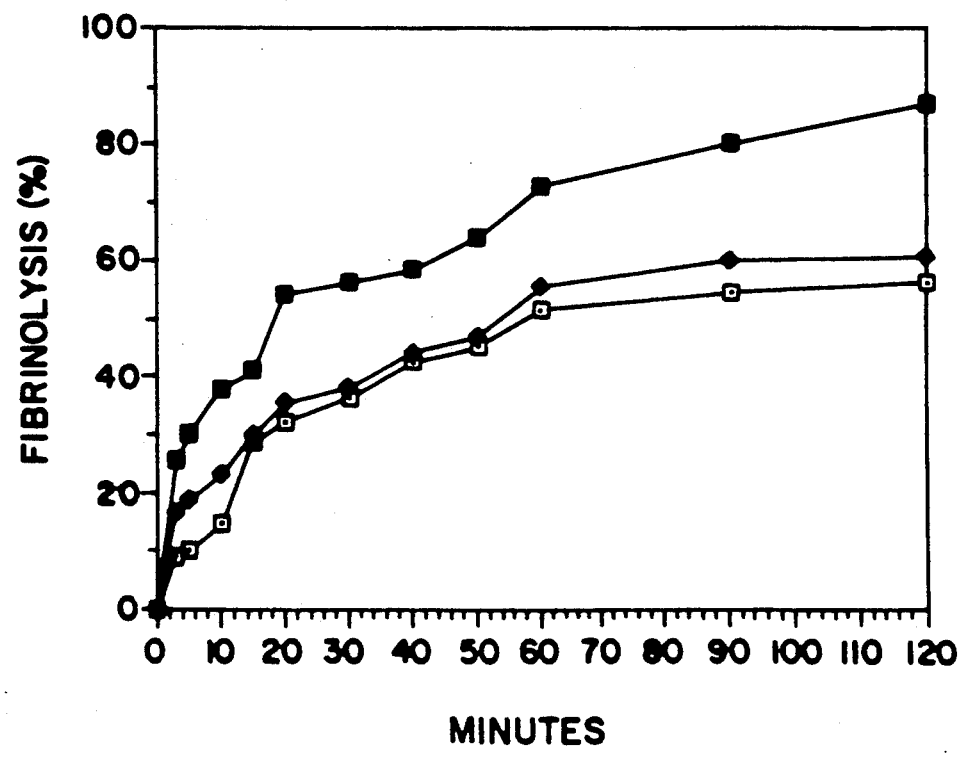

The results are shown in the accompanying FIGS. 4 and 5 wherein there are shown in average of twice tests.

FIG. 4 shows the results in the thrombosis prepared by using blood collected from one person, wherein the symbol -□- is the data obtained in the addition of urokinase alone without exposure of ultrasound, -◆- is the data obtained in the addition of urokinase alone with exposure of ultrasound, and -■- is the data obtained in the addition of a mixture of urokinase and the booster with exposure of ultrasound.

As is shown in FIG. 4, the time for achieving 20% fibrinolysis was 45 minutes by urokinase alone without exposure of ultrasound, 30 minutes by a combination of urokinase and exposure of ultrasound, and only 10 minutes by a combination of a mixture of urokinase and a booster and exposure of ultrasound. The fibrinolytic effects of urokinase (both the rate of fibrinolysis and the fibrinlytic time) were signigicantly enhanced by using a booster with application of ultrasound.

FIG. 5 shows the results in the thrombosis prepared by using blood collected from another person and with reduced energy of ultrasound by 15%, wherein the symbols are the same as in FIG. 4. As is shown in FIG. 5, the fibrinolytic effects were significantly enhanced by using a mixture of urokinase and the booster. That is, in case of using urokinase alone with exposure of ultrasound, the 50% fibrinolysis was achieved by the treatment for 60 minutes, but in case of using a mixture of urokinase and the booster with exposure of ultrasound, it reduced to one fourth, i.e. it was achieved by the treatment only for 15 minutes.

What is claim is:

1. A booster for enhancing effects of ultrasound in the therapy of diseases, which comprises:
   a. a medicament and
   b. microbubbles of a gas having a diameter of 0.1 to 100 μm in a liquid.

2. The booster according to claim 1, wherein the microbubbles are formed from air or oxygen gas in the liquid.

3. The booster according to claim 1, wherein the liquid is a 3 to 5% human serum albumin solution.

4. A pharmaceutical liquid composition for the therapy of diseases with application of ultrasound, which comprises:
   a. microbubbles of a gas having a diameter of 0.1 to 100 μm and
   b. a medicament selected from the group consisting of thrombolytic agents, hormones, antibiotics and antineoplastic agents in a liquid.

5. The composition according to claim 4, wherein the microbubbles are formed from air or oxygen gas in the liquid.

6. The composition according to claim 4, wherein the liquid is a 3 to 5% human serum albumin solution.

7. The composition according to claim 4, wherein the medicament is a member selected from thromobolytic agents, hormones, antibiotics, and antineoplastic agents.

8. The composition according to claim 4, wherein the medicament is selected from the group consisting of urokinase, tissue plasminogen activator, insulin, theophylline, and lidocaine.

9. A method for enhancing the therapeutic effects of a medicament, comprising:
   a. applying ultrasound to a pharmaceutical liquid composition according to claim 4 and
   b. administering said pharmaceutical liquid composition.

10. The method according to claim 9, wherein the liquid composition comprises about $4 \times 10^7$ cells/ml of microbubbles of a gas having a diameter of 0.1 to 100 μm and a medicament in the liquid.

11. The method according to claim 10, wherein the liquid is a 3 to 5% human serum albumin solution.

12. The method according to claim 9, wherein the medicament is selected from the group consisting of urokinase, tissue plasminogen activator, insulin, theophylline, and lidocaine.

13. A method of dosing subjects with a pharmaceutical preparation by:
   a. applying ultrasound to a pharmaceutical liquid composition and
   b. administering said pharmaceutical liquid composition comprising microbubbles of a gas having a diameter of 0.1 to 100 μm and a medicament in a liquid in the therapy of diseases.

14. The method of dosing according to claim 13, wherein the microbubbles are formed from air or oxygen gas in the liquid.

15. The method of dosing according to claim 13, wherein the liquid is a 3 to 5% human serum albumin solution.

16. The method of dosing according to claim 13, wherein the medicament is selected from the group consisting of urokinase, tissue plasminogen activator, insulin, theophylline, and lidocaine.

* * * * *